(12) United States Patent
Searle et al.

(10) Patent No.: US 6,436,869 B1
(45) Date of Patent: Aug. 20, 2002

(54) IRON, COBALT AND/OR NICKEL CONTAINING ALPO BOUND SAPO MOLECULAR SIEVE CATALYST FOR PRODUCING OLEFINS

(75) Inventors: Ronald G. Searle, Houston; Krishna K. Rao, Kingwood; Gary D. Mohr; Xiaobing Feng, both of League City, all of TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/517,546

(22) Filed: Mar. 2, 2000

Related U.S. Application Data

(60) Continuation-in-part of application No. 09/328,724, filed on Jun. 9, 1999, now abandoned, which is a division of application No. 08/865,635, filed on May 29, 1997, now Pat. No. 5,972,203.
(60) Provisional application No. 60/018,546, filed on May 29, 1996.

(51) Int. Cl.[7] .............................................. B01J 27/182
(52) U.S. Cl. ...................................... 502/214; 502/208
(58) Field of Search .................................. 502/208, 214

(56) References Cited

U.S. PATENT DOCUMENTS

| | | | |
|---|---|---|---|
| 3,244,766 A | 4/1966 | Keough | |
| 3,258,455 A | 6/1966 | Natta et al. | |
| 3,305,538 A | 2/1967 | Natta et al. | |
| 3,364,190 A | 1/1968 | Emrick | |
| 3,645,992 A | 2/1972 | Elston | |
| 4,025,576 A | 5/1977 | Chang et al. | |
| 4,068,136 A | 1/1978 | Minami | 307/353 |
| 4,076,698 A | 2/1978 | Anderson et al. | 526/348.6 |
| 4,243,691 A | 1/1981 | Mohlenkamp, Jr. et al. | 426/649 |
| 4,302,565 A | 11/1981 | Goeke et al. | 526/88 |
| 4,440,871 A | 4/1984 | Lok et al. | 502/214 |
| 4,499,327 A | 2/1985 | Kaiser | 585/640 |
| 4,659,685 A | 4/1987 | Coleman, III et al. | 502/113 |
| 4,677,242 A | 6/1987 | Kaiser | 585/638 |
| 4,677,243 A | 6/1987 | Kaiser | 585/638 |
| 4,752,651 A | 6/1988 | Kaiser | 585/640 |
| 4,814,316 A * | 3/1989 | Pellet et al. | 502/214 |
| 4,861,743 A | 8/1989 | Flank et al. | 502/214 |
| 4,861,938 A | 8/1989 | Lewis et al. | 585/640 |
| 4,943,424 A | 7/1990 | Miller | 423/328 |
| 5,095,163 A | 3/1992 | Barger | 585/640 |
| 5,096,684 A | 3/1992 | Guth et al. | 423/306 |
| 5,126,308 A | 6/1992 | Barger et al. | 502/214 |
| 5,191,141 A | 3/1993 | Barger et al. | 585/640 |
| 5,233,117 A | 8/1993 | Barger | 585/640 |
| 5,278,345 A | 1/1994 | Janssen et al. | 585/640 |
| 5,279,810 A | 1/1994 | Calabro | 423/701 |
| 5,324,493 A | 6/1994 | Mueller et al. | 423/311 |
| 5,460,796 A | 10/1995 | Verduijn | 423/700 |
| 5,475,182 A | 12/1995 | Janssen | 585/640 |
| 5,663,471 A | 9/1997 | Kvisle et al. | 585/639 |
| 5,714,662 A | 2/1998 | Vora et al. | 585/640 |
| 5,714,663 A | 2/1998 | Serrand et al. | 585/648 |
| 5,892,079 A | 4/1999 | Wilson, Jr. | 556/11 |
| 5,904,880 A | 5/1999 | Sun | |
| 5,907,076 A | 5/1999 | Ou et al. | 585/800 |
| 5,912,393 A | 6/1999 | Barger et al. | 585/640 |
| 5,925,586 A | 7/1999 | Sun | 502/62 |
| 5,925,800 A | 7/1999 | Sun et al. | 585/640 |
| 5,927,063 A | 7/1999 | Janda et al. | 60/39.02 |
| 5,932,512 A | 8/1999 | Sun | 502/214 |
| 5,952,538 A | 9/1999 | Vaughn et al. | 585/640 |
| 5,960,643 A | 10/1999 | Kuechler et al. | 62/620 |
| 5,962,762 A | 10/1999 | Sun et al. | 585/640 |
| 5,972,203 A | 10/1999 | Smith et al. | 208/113 |
| 6,004,898 A | 12/1999 | Sun | 502/214 |
| 6,005,155 A | 12/1999 | Sun | 585/640 |
| 6,023,005 A | 2/2000 | Lattner et al. | 585/639 |
| 6,034,020 A | 3/2000 | Drake et al. | 502/60 |
| 6,040,257 A | 3/2000 | Drake et al. | 502/64 |
| 6,040,259 A * | 3/2000 | Mohr et al. | 502/67 |
| 6,040,264 A | 3/2000 | Sun et al. | 502/214 |
| 6,046,371 A | 4/2000 | Wu et al. | 585/638 |
| 6,046,373 A | 4/2000 | Sun | 585/640 |
| 6,051,745 A | 4/2000 | Wu et al. | 585/638 |
| 6,051,746 A | 4/2000 | Sun et al. | 585/639 |
| 6,057,261 A | 5/2000 | Sun | 502/341 |

FOREIGN PATENT DOCUMENTS

| EP | 0293926 | * 12/1988 |
|---|---|---|
| EP | 0293937 | * 12/1988 |

OTHER PUBLICATIONS

Barger et al., "Converting Natural Gas to Ethylene and Propylene by the UOP/Hydro MTO Process," 12th International Zeolite Conference 1999 Materials Research Society pp. 567–573, no month.

Blackwell et al., "Solid–State NMR of Silicoaluminophosphate Molecular Sieves and Aluminophosphate Materials," J. Phys. Chem., 92, 3965–3970 (1988), no month.

Chang, "Methanol Conversion to Light Olefins," Catal. Rev.–Sci. Eng., 26(3&4), 323–345 (1984), no month.

Dahl et al., "Structural and chemical influences on the MTO reaction: a comparison of chabazite and SAPO–34 as MTO catalysts," Microporous and Mesoporous Materials 29 (1999) 185–190, no month.

(List continued on next page.)

Primary Examiner—Elizabeth D. Wood

(57) ABSTRACT

An aluminophosphate bound silicoaluminophosphate catalyst contains iron, cobalt and/or nickel is useful in a method of making a product including an olefin from a feedstock containing an oxygenate. The method includes contacting an oxygenate feedstock with the catalyst, which is an aluminophosphate bound silicoaluminophosphate catalyst containing iron, cobalt and/or nickel and which does not contain a significant amount of amorphous binder, in its activated state under conditions effective to produce an olefin product.

4 Claims, No Drawings

OTHER PUBLICATIONS

DeChen et al., "The effect of crystal size of SAPO–34 on the selectivity and deactivation of the MTO reaction," Microporous and Mesoporous Materials 29 (1999) 191–203, no month.

Kaeding et al., "Production of Chemicals from Methanol," Journal of Catalysis 61, 155–164 (1980), no month.

Prakash, A.M., "Synthesis of SAPO–34: High Silicon Incorporation in the Presence of Morpholine as Template," J. Chem. Soc., Faraday Tans., 1994, 90(15), 2291–2296, no month.

Scherzer, Julius, "VI. Selected Preparation and Manufacturing Process for FCC Catalysts," *Octane–Enhancing Zeolitic FCC Catalysts; Scientific and Technical Aspects*, (Marcel Dekker, Inc. New York, 1990), no month.

Wilson et al., "The characteristics of SAPO–34 which influence the conversion of methanol to light olefins," Microporous and Mesoporous Materials 29 (1999) 117–116, no month.

\* cited by examiner

IRON, COBALT AND/OR NICKEL CONTAINING ALPO BOUND SAPO MOLECULAR SIEVE CATALYST FOR PRODUCING OLEFINS

This is a continuation-in-part application of U.S. Ser. No. 09/328,724 filed Jun. 9, 1999, and now abandoned, which in turn is a divisional application of U.S. Ser. No. 08/865,635, filed May 29, 1997, now U.S. Pat. No. 5,972,203, which claims priority on U.S. Provisional Appl. Ser. No. 60/018, 546 filed May 29, 1996, the contents of each of which are incorporated herein by reference in their entirety.

FIELD OF THE INVENTION

This invention relates to a catalyst and a method for converting an oxygenate feedstock to an olefin product. In particular, this invention is directed to a method for converting an oxygenate feedstock to an olefin product by contacting the feedstock with an aluminophosphate (ALPO) bound silicoaluminophosphate (SAPO) catalyst containing iron, cobalt and/or nickel, which can be tailored to optimize its performance.

BACKGROUND OF THE INVENTION

Olefins have traditionally been produced through the process of petroleum cracking. Because of the limited availability and high cost of petroleum sources, the cost of producing olefins from such petroleum sources has the potential to steadily increase. Light olefins such as ethylene and propylene serve as feeds for the production of numerous chemicals and polymers.

The search for alternative materials for the production of light olefins such as ethylene and propylene has led to the use of oxygenates such as alcohols, and more particularly to methanol and ethanol or their derivatives as feedstocks. These and other alcohols may be produced by fermentation or from synthesis gas. Synthesis gas can be produced from natural gas, petroleum liquids, carbonaceous materials including coal, recycled plastics, municipal wastes, or any organic material. Thus alcohols and alcohol derivatives may provide non-petroleum based routes for hydrocarbon production.

Silicoaluminophosphates (SAPOs) are structured crystalline molecular sieves which have found application as catalysts. In particular, the use of SAPOs in converting alcohols or ethers to olefin products, particularly ethylene and propylene, is becoming of greater interest for large scale, commercial production facilities.

In contrast to SAPOs, an aluminophosphate ($AlP_4$) framework inherently is neutral in electrical charges. The incorporation of silicon or other metallic or nonmetallic elements into the framework by substitution generates more active catalytic sites, particularly acid sites, and increased acidity. Thus, non-acidic aluminophosphates (ALPOs) lack silicon or another substituent that generates acidic charges.

Oxygenates are a promising alternative feedstock for making light olefins. Particularly promising oxygenate feedstocks are alcohols, such as methanol and ethanol, dimethyl ether, methyl ethyl ether, diethyl ether, dimethyl carbonate, and methyl formate. Many of these oxygenates can be produced by fermentation, or from synthesis gas derived from natural gas, petroleum liquids, carbonaceous materials, including coal, recycled plastics, municipal wastes, or any appropriate organic material. Because of the wide variety of sources, alcohol, alcohol derivatives, and other oxygenates have promise as an economical, non-petroleum source for light olefin production. SAPOs and zeolites are catalysts known to convert oxygenates to light olefins.

With regard to zeolites, for example, U.S. Pat. No. 3,244, 766 to Keough teaches a process for ethanol conversion to ethylene with a hydrogen exchanged mordenite catalyst. Keough discloses that such catalyst allows the dehydration of alcohol to occur at temperatures below 300° C.

U.S. Pat. No. 4,025,576 to Chang et al. teaches a multistage process for converting light alcohols to olefins using certain crystalline zeolites having a high silica:alumina ratio and a constrained access to the crystalline space, for example HZSM-5. Cheng et al. indicate that a critical feature of the invention, namely conducting the conversion from alcohol to olefin at subatmospheric partial pressure of the reactant feed and using certain crystalline zeolites, enhances selectivity for olefin production and permits complete conversion of the alcohol.

Zeolite-bound zeolites, also described as binderless zeolites, have also been used to convert oxygenates to olefins. U.S. Pat. No. 5,460,796 to Verduijn et al. discloses a substantially binderless zeolite produced by an aging process that substantially converts the silica binder to zeolite having mechanical strength that is comparable to and perhaps stronger than that of silica-bound zeolite aggregate.

SAPOs are also known as being useful in methanol to olefin conversions. For example, U.S. Pat. No. 4,499,327 to Kaiser et al. discloses a process for converting methanol to olefins (MTO) using non-zeolitic molecular sieves such as SAPO-34.

One problem with SAPO catalysts is the presence of acid sites on the external surface thereof that are not shape selective. Thus, the external acid sites can adversely affect product yields. Further, amorphous (non-molecular sieve) binders that are frequently used to bind SAPO molecular sieves are thought to reduce the access of the pores of the SAPO during the conversion of oxygenates to olefins. A need exists in the art for a catalyst that retains the favorable aspects of SAPO catalysts but that eliminates the problems caused by the external acid sites on the catalyst and pore accessibility.

Moreover, in converting a feedstock containing an oxygenate to a product including an olefin, better selectivity to product, as well as away from undesirable by-product, is still needed. It is particularly desirable to obtain product high in ethylene and/or propylene content, while reducing the amount of any one or more of the $C_1$–$C_4$ paraffin by-products and to reduce the amount of coke deposits on the catalyst during the reaction.

SUMMARY OF THE INVENTION

In order to overcome various problems presently inherent in the art, this invention provides various embodiments of a catalyst and a method for continuous production of olefin product from an oxygenate-containing feedstock. In one embodiment, a catalyst comprises SAPO crystals, a binder comprising ALPO crystals, and nickel, cobalt and/or iron, wherein the catalyst does not contain significant amounts of amorphous binder, but rather contains crystalline ALPO. The catalyst preferably contains less than 10% by weight of amorphous binder based on weight of the SAPO and the ALPO, more preferably less than 5%, and most preferably the catalyst is substantially free of amorphous binder.

The catalyst is prepared by a process comprising preparing a SAPO framework; removing a template from the SAPO framework; preparing an alumina-bound SAPO from the detemplated SAPO framework and amorphous alumina;

converting the amorphous alumina to crystalline ALPO to provide an ALPO-bound SAPO; and incorporating iron, cobalt, and/or nickel into the catalyst after the removing step or after the converting step.

In another embodiment, the method of making olefins comprises providing an ALPO bound SAPO catalyst containing iron, cobalt and/or nickel; and contacting the catalyst with the feedstock containing an oxygenate under conditions effective to convert the feedstock containing an oxygenate to a product including an olefin. In a particular embodiment, the invention is directed to an olefin prepared by this process. Such olefins can be further processed by contacting the olefin product with a polyolefin-forming catalyst under conditions effective to form a polyolefin. Alternatively, such olefins can be recovered from the product to prepare an olefin derivative preferably selected from the group consisting of aldehyde, alcohol, acetic acid, linear alpha olefins, vinyl acetate, ethylene dichloride, vinyl chloride, ethyl benzene, ethylene oxide, cumene, isopropyl alcohol, acrolein, allyl chloride, propylene oxide, acrylic acid, ethylene rubber, propylene rubber, acrylonitrile, a dimer of ethylene, propylene or butylene, and a trimer of ethylene, propylene or butylene.

Iron, cobalt and/or nickel is incorporated into the SAPO portion of the ALPO bound SAPO. The iron, cobalt and/or nickel containing ALPO bound SAPO catalyst is of great benefit in large scale commercial processes of making olefin product from oxygenate feedstock, particularly making olefins containing ethylene or propylene from feedstock comprising methanol or dimethyl ether. The presence of iron, cobalt and/or nickel increases the selectivity of ethylene and/or propylene in comparison with SAPO and reduces the byproducts formed during the olefin conversion process. Thus, the catalyst of the present invention finds particular application in oxygenate conversion processes where catalyst acidity in combination with crystalline structure, as well as high selectivity for ethylene and/or propylene, are important for reaction selectivity.

In the embodiments, the SAPO crystals have an average particle size greater than about 0.1 micron, preferably 0.1 to about 15 microns, and more preferably 1 to 6 microns. Preferably, the ALPO crystals have an average particle size that is less than the SAPO crystals. The ALPO crystals preferably have an average particle size of less than 1 micron, and more preferably about 0.1 to about 0.5 microns. The ALPO crystals are intergrown and form at least a partial coating on the SAPO crystals.

In the embodiments, the silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrowths and mixtures thereof, and preferably SAPO-17, SAPO-18, SAPO-34, SAPO-35, SAPO-44, SAPO-47 and mixtures and intergrowths thereof.

In the embodiments, the aluminophosphate coating is preferably selected from the group consisting of ALPO-41, ALPO-5, ALPO-11, ALPO-17, ALPO-18, ALPO-19, and ALPO-34, and more preferably ALPO-17, ALPO-18, ALPO-11, ALPO-5, and ALPO-34. Preferably, the ALPO crystals are present in an amount in the range of from about 10 to about 60% by weight based on the weight of the SAPO. The ALPO crystals are not acidic, which enhances the performance of the catalyst. Further, the structure type of the non-amorphous ALPO crystals can be selected so that it does not significantly adversely affect the reactants exiting the pores of the SAPO. The SAPO and the ALPO can have the same or different structure types. ALPO's crystal structure allows oxygenates to have increased access to the pores of the SAPO during olefin conversion, in comparison to amorphous (non-molecular sieve) binders.

The oxygenate feedstock is preferably selected from the group consisting of methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof More preferably, the oxygenate feedstock is methanol, dimethyl ether or a mixture thereof In order to convert the oxygenate to olefin product, the process is preferably performed at a temperature between 200° C. and 800° C.

DETAILED DESCRIPTION IF THE INVENTION

The catalyst of the present invention comprises SAPO crystals, iron, cobalt and/or nickel, and a binder comprising ALPO crystals. The ALPO crystals are the main binder ingredient in the catalyst, which give mechanical strength to the SAPO. In contrast, conventional SAPO catalysts used in hydrocarbon conversion processes are normally bound with silica or alumina or other commonly used amorphous (non-molecular sieve) binders to enhance the mechanical strength of the SAPO.

The silicoaluminophosphate molecular sieves of this invention comprise a three-dimensional microporous crystal framework structure of $[SiO_2]$, $[AlO_2]$ and is $[PO_2]$ corner sharing tetrahedral units. The way Si is incorporated into the structure can be determined by $^{29}Si$ MAS NMR. See Blackwell and Patton, J. Phys. Chem., 92, 3965 (1988). The desired SAPO molecular sieves will exhibit one or more peaks in the $^{29}Si$ MAS NMR, with a chemical shift $\delta(Si)$ in the range of –88 to –94 ppm and with a combined peak area in that range of at least 20% of the total peak area of all peaks with a chemical shift $\delta(Si)$ in the range of –88 ppm to –115 ppm, where the $\delta(Si)$ chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These preferred pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [$SiO_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and mixtures thereof Preferred are SAPO-17, SAPO-18, SAPO-34, SAPO-35, SAPO-44, and SAPO-47, particularly SAPO-18 and SAPO-34, and mixtures thereof As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product is formed in solution. It can be recovered by standard means, however, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed to obtain catalytic activity. Once the template is removed, the crystalline structure that remains has what is typically called an intracrystalline pore system.

The SAPO molecular sieve can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof Preferred templates are triethylamine, cyclohexylamine, piperidine, pyridine, isopropylamine, tetraethyl ammonium salts, and mixtures thereof The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

Unlike typical crystalline molecular sieve catalysts used in hydrocarbon conversion processes which are normally bound with silica or alumina or other commonly used amorphous (non-molecular sieve) binders to enhance its mechanical strength, the ALPO bound catalyst of the present invention generally does not contain significant amounts of amorphous binders. Specifically, a significant amount refers to catalysts that contain less than 10 percent by weight, based on the combined weight of the SAPO and ALPO, of non-crystalline molecular sieve binder. More preferably, a catalyst contains less than 5 percent by weight, and, most preferably, the catalyst is substantially free of non-crystalline molecular sieve binder. Preferably, the ALPO crystals bind the SAPO crystals by adhering to the surface of the SAPO crystals thereby forming a matrix or bridge structure which also holds the first crystals particles together. More preferably, the ALPO particles bind the SAPO by intergrowing so as to form a coating or partial coating on the larger SAPO crystals and, most preferably, the ALPO crystals bind the SAPO crystals by intergrowing to form an attrition resistant over-growth over the SAPO crystals.

The ALPO preferably is substantially non-acidic. The preferred non-acidic ALPOs include ALPO-17, ALPO-18, ALPO-11, ALPO-5, and ALPO-34. The pore size of the ALPO will preferably be a pore size that does not significantly restrict access of the hydrocarbon feedstream to the pores of the SAPO. For instance, when the materials of the feedstream which are to be converted have a size from 5 § to 6.8 §, the ALPO will preferably be a large pore size, that is, greater than about 7 §, or an intermediate pore size ALPO, that is, from about 7 § to about 5 §.

The terms "acidity", "lower acidity" and "higher acidity" as applied to crystalline molecular sieve are known to persons skilled in the art. The acidic properties of crystalline molecular sieves are well known. However, with respect to the present invention, a distinction must be made between acid strength and acid site density. Acid sites of a crystalline molecular sieves such as SAPO can be a Bronsted acid and/or a Lewis acid. The density of the acid sites and the number of acid sites are important in determining the acidity of the SAPO. Factors directly influencing the acid strength are (i) the chemical composition of the SAPO framework, i.e., relative concentration and type of tetrahedral atoms, (ii) the concentration of the extra-framework cations and the resulting extra-framework species, (iii) the local structure of the SAPO, e.g., the pore size and the location, within the crystal or at/near the surface of the SAPO, and (iv) the pretreatment conditions and presence of co-adsorbed molecules. As used herein, the terms "acidity", "lower acidity" and "higher acidity" refers to the concentration of acid sites regardless of the strength of such acid sites which can be measured by ammonia absorption.

The ALPO is preferably present in the catalyst in an amount in the range of from about 10 to about 60% by weight based on the weight of the SAPO but the amount of ALPO present will usually depend on the hydrocarbon process in which the catalyst is utilized. More preferably, the amount of ALPO present is in an amount of from about 20 to about 50% by weight.

The term "average particle size" as used herein, means the arithmetic average of the diameter distribution of the crystals on a volume basis. The ALPO crystals preferably have a smaller size than the SAPO crystals. The average particle size of the SAPO crystals is preferably from about 0.1 to about 15 microns. In many applications, the average particle size is preferably from about 1 to about 6 microns. The ALPO crystals preferably have an average particle size of less than 1 micron, preferably from about 0.1 to less than 0.5 micron. The ALPO crystals, in addition to binding the SAPO particles and maximizing the performance of the catalyst will preferably intergrow and to form an over-growth which coats or partially coats the SAPO. Preferably, the coating will be resistant to attrition.

The ALPO bound SAPO, that is SAPO that is bound by a crystalline ALPO, is preferably prepared by a three step procedure. The first step involves the synthesis of the SAPO. Processes for preparing the SAPO are known in the art. Before proceeding to the next step, the SAPO template must be removed. The removal process is typically accomplished by calcining, or essentially heating the template at a temperature of from 200° C. to 800° C. in the presence of an oxygen-containing gas. In some cases, it may be desirable to heat in an environment having a low oxygen concentration.

In the next step, an alumina-bound SAPO is prepared preferably by mixing a mixture comprising the calcined SAPO crystals, alumina, water and optionally an extrusion aid until a homogeneous composition in the form of an extrudable paste develops. An alumina-bound SAPO is simply a SAPO that is bound by an amorphous alumina binder. The alumina binder used in preparing the alumina bound SAPO aggregate is preferably an alumina sol. The amount of SAPO in the extrudate when dry will range from about 30 to 90% by weight, more preferably from about 40 to 90% by weight, with the balance being primarily alumina, e.g., about 10 to 60% by weight alumina.

The resulting paste is then molded, e.g. extruded, and cut into small strands, e.g., approximately 2 mm diameter extrudates, which are dried at 100–150° C. for a period of 4–12 hours. Preferably the dried extrudates are then calcined in air at a temperature of from about 400° C. to 550° C. for a period of from about 1 to 10 hours. This calcination step also destroys the extrusion aid if present.

Optionally, the alumina-bound aggregate can be made into a very small crystals which have application in fluid bed processes such as catalytic cracking. This preferably involves mixing the SAPO with an alumina-containing matrix solution so that an aqueous solution of SAPO and alumina binder is formed which can be sprayed dried to result in small fluidizable alumina-bound aggregate crystals. Procedures for preparing such aggregate crystals are known to persons skilled in the art. An example of such a procedure is described by Scherzer (Octane-Enhancing Zeolitic FCC Catalysts, Julius Scherzer, Marcel Dekker, Inc. New York, 1990). The fluidizable alumina-bound aggregate crystals, like the alumina bound extrudates described above, would then undergo the final step described below to convert the alumina binder to an ALPO.

The third step in the three step ALPO bound SAPO preparation process is the conversion of the alumina present in the alumina-bound catalyst to an ALPO which serves to bind the residual SAPO crystals together. To prepare the catalyst, the alumina-bound aggregate is preferably first aged in an appropriate aqueous solution at elevated temperature. Next, the contents of the solution and the temperature at which the aggregate is aged should be selected to convert the amorphous alumina binder into an ALPO. The newly-formed ALPO is produced as crystals. The crystals may grow on and/or adhere to the SAPO crystals, and may also be produced in the form of new intergrown crystals, which are generally much smaller than the initial crystals, e.g., of sub-micron size. These newly formed crystals may grow together and interconnect thereby causing the larger crystals to become bound together.

The nature of the ALPO formed in the secondary synthesis conversion of the alumina to ALPO may vary as a function of the composition of the secondary synthesis solution and synthesis aging conditions. The secondary synthesis solution is an aqueous ionic solution containing a source of phosphoric acid and a templating agent sufficient to convert the alumina to the desired ALPO.

As is known in the art, a catalyst containing a molecular sieve, must be activated prior to use in a catalytic process. Activation is performed in such a manner that template is removed from the molecular sieve, leaving active catalytic sites with the microporous channels of the molecular sieve open for contact with feed. The activation process is typically accomplished by calcining, or essentially heating the template at a temperature of from 200 to 800° C. in the presence of an oxygen-containing gas. In some cases, it may be desirable to heat in an environment having a low oxygen concentration. This type of process can be used for partial or complete removal of the template from the intracrystalline pore system. In other cases, particularly with smaller templates, complete or partial removal from the sieve can be accomplished by conventional desorption processes such as those used in making standard zeolites.

Iron, cobalt and/or nickel can be incorporated into the ALPO bound SAPO catalyst through any one of the standard methods well known to whose skilled in the art, for example by ion-exchange or impregnation. Iron, cobalt and/or nickel can be incorporated into the catalyst either after the calcined SAPO crystals are formed or after the calcined ALPO crystals, which are bound to the calcined SAPO crystals, are formed. The iron, cobalt and/or nickel SAPO portion of the catalyst represents the active portion of the catalyst when used in the process to convert oxygenates to olefins.

In one embodiment, iron, cobalt and/or nickel is incorporated by ion exchange. In an ion exchange process, a solution of iron, cobalt and/or nickel is first made by dissolving the desired amount of a iron, cobalt and/or nickel-containing compound in water under mild conditions. Preferably the water is de-ionized. The temperature of mixing is dependent upon the iron, cobalt and/or nickel-containing compound's solubility in water, or whatever other medium is selected. The process may be conducted under pressure or at atmospheric pressure. After adequate mixing, the solution is then added to the selected amount of the ALPO bound SAPO. The resulting mixture is stirred as required. In some cases, stirring is not required and the mixture may be left undisturbed for a time adequate to permit the desired level of incorporation. The catalyst product is then filtered, optionally washed, dried, and calcined by methods well known to those skilled in the art.

In another embodiment, iron, cobalt and/or nickel is impregnated into the SAPO molecular sieve.

The amount of iron, cobalt and/or nickel which is incorporated into the catalyst may vary over a wide range depending, at least in part, on the selected catalyst and the incorporation method. The amount of iron, cobalt and/or nickel incorporated is measured on an atomic basis in terms of a silicon to iron, cobalt and/or nickel ratio. The silicon to iron, cobalt and/or nickel ratios are in the range from about 0.01:1 to about 1000:1, preferably from about 0.1:1 to about 500:1, and most preferably from about 0.5:1 to 50:1.

Additional olefin-forming molecular sieve materials can be mixed with the silicoaluminophosphate catalyst if desired. Several types of molecular sieves exist, each of which exhibit different properties. Structural types of small pore molecular sieves that are suitable for use in this invention include AEI, AFT, APC, ATN, ATT, ATV, AWW, BIK, CAS, CHA, DDR, EDI, ERI GOO, KFI, LEV, LTA, MON, PAU, PHI, RHO, THO, and substituted forms thereof Structural types of medium pore molecular sieves that are suitable for use in this invention include MFI, MEL, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

In one embodiment of this invention, a feed containing an oxygenate is contacted in a reaction zone of a reactor apparatus with an activated iron, cobalt and/or nickel containing ALPO bound SAPO catalyst at process conditions effective to produce light olefins, i.e., an effective temperature, pressure, WHSV (weight hour space velocity) and, optionally, an effective amount of diluent, correlated to produce light olefins. Typically, the oxygenate feed is contacted with the catalyst when the oxygenate is in a vapor phase. However, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 600° C. is preferred.

Owing to the nature of the process, it may be desirable to carry out the process of the present invention by use of the molecular sieve catalysts in a dynamic bed system or any system of a variety of transport beds rather than in a fixed bed system. It is particularly desirable to operate the reaction process at high space velocities.

The conversion of oxygenates to produce light olefins may be carried out in a variety of large scale catalytic reactors, including, but not limited to, fluid bed reactors and concurrent riser reactors as described in "Free Fall Reactor," Fluidization Engineering, D. Kunii and O. Levenspiel, Robert E. Krieger Publishing Co. N.Y., 1977, incorporated in its entirety herein by reference. Additionally, countercurrent free fall reactors may be used in the conversion process. See, for example, U.S. Pat. No. 4,068,136 and "Riser Reactor", Fluidization and Fluid-Particle Systems, pages 48–59, F. A. Zenz and D. F. Othmo, Reinhold Publishing Corp., N.Y. 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 $hr^{-1}$ to 1000 $hr^{-1}$. In the case of commercial scale reactors, WHSV is defined as the weight of hydrocarbon in the feed per hour per weight of silicoaluminophosphate molecular sieve content of the catalyst. The hydrocarbon content will be oxygenate and any hydrocarbon which may optionally be combined with the oxygenate. The silicoaluminophosphate molecular sieve content is intended to mean only the silicoaluminophosphate molecular sieve portion that is contained within the catalyst. This excludes components such as binders, diluents, inerts, rare earth components, etc.

It is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in °C.:

$$TCNMS = \frac{NMS}{1 + (((T - 400)/400) \times 14.84}$$

The pressure also may vary over a wide range, including autogenous pressures. Effective pressures may be in, but are not necessarily limited to, pressures of from about 0.1 kPa to about 10 MPa. Preferred pressures are in the range of about 5 kPa to about 5 MPa, with the most preferred range being of from about 50 kPa to about 0.5 MPa. The foregoing pressures are exclusive of any oxygen depleted diluent, and thus, refer to the partial pressure of the oxygenate compounds and/or mixtures thereof with feedstock. At the lower and upper end of the foregoing pressure ranges, the rate of selectivity, conversion and/or reaction may not be optimum.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to, helium, argon, nitrogen, carbon monoxide, carbon dioxide, hydrogen, water, paraffins, alkanes (especially methane, ethane, and propane), alkylene, aromatic compounds, and mixtures thereof The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, and carbonyl compounds (e.g., aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

Ethylene and propylene are selectively produced from an oxygenate using the catalyst according to the invention. Such selectivity of ethylene plus propylene is from 50–95% of the hydrocarbon content of the feed.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

Having now fully described this invention, it will be appreciated by those skilled in the art that the invention can be performed within a wide range of parameters within what is claimed, without departing from the spirit and scope of the invention

What is claimed is:

1. A process for making a catalyst comprising:

mixing calcined SAPO crystals with an alumina binder to form an alumina-bound SAPO;

converting a portion of the alumina binder in the alumina-bound SAPO to provide an ALPO-bound SAPO; and incorporating iron, cobalt, and/or nickel into the alumina-bound SAPO or into the calcined SAPO crystals.

2. The method recited in claim 1, wherein converting a portion of the alumina binder comprises adding phosphoric acid, templating agent, and water to the heated extrudates to form an aqueous solution, and heating the aqueous solution at an elevated temperature.

3. A method for making a SAPO molecular sieve catalyst comprising:

mixing SAPO crystals with an alumina binder to form an alumina-SAPO mixture;

drying the alumina-SAPO mixture to form an alumina-SAPO aggregate;

converting a portion of the alumina in the alumina-SAPO aggregate to ALPO crystals; and incorporating iron, cobalt, and/or nickel into the alumina-bound SAPO or into the calcined SAPO crystals.

4. The method of claim 3 further comprising adding phosphoric acid, templating agent, and water to the alumina-SAPO aggregate to form an aqueous solution, and heating the aqueous solution to convert the portion of the alumina in the alumina-SAPO aggregto ALPO crystals.

* * * * *